(12) United States Patent
Kang

(10) Patent No.: US 10,145,549 B2
(45) Date of Patent: Dec. 4, 2018

(54) CANDLE WARMER HAVING TOUCH TYPE ON/OFF MEANS

(71) Applicant: LEPANTO CO., LTD., Seoul (KR)

(72) Inventor: Ji Yun Kang, Seoul (KR)

(73) Assignee: LEPANTO CO., LTD, Seoul (KR)

( * ) Notice: Subject to any disclaimer, the term of this patent is extended or adjusted under 35 U.S.C. 154(b) by 0 days.

(21) Appl. No.: 15/578,634

(22) PCT Filed: Nov. 20, 2015

(86) PCT No.: PCT/KR2015/012555
§ 371 (c)(1),
(2) Date: Nov. 30, 2017

(87) PCT Pub. No.: WO2016/199990
PCT Pub. Date: Dec. 15, 2016

(65) Prior Publication Data
US 2018/0156434 A1    Jun. 7, 2018

(30) Foreign Application Priority Data
Jun. 8, 2015  (KR) .................. 10-2015-0080543

(51) Int. Cl.
*F21V 7/04*    (2006.01)
*F21L 17/00*   (2006.01)
(Continued)

(52) U.S. Cl.
CPC .......... *F21V 23/0485* (2013.01); *F21L 17/00* (2013.01); *F21L 19/00* (2013.01);
(Continued)

(58) Field of Classification Search
None
See application file for complete search history.

(56) References Cited

U.S. PATENT DOCUMENTS 6,354,710 B1 *  3/2002  Nacouzi ............... A61L 9/03
                                                       219/220
2003/0209533 A1   11/2003  Tanner et al.

FOREIGN PATENT DOCUMENTS

KR      20-0219364 Y1    4/2001
KR   20-2008-0005453 U   11/2008
(Continued)

OTHER PUBLICATIONS

Blog post of "Market B Touch Candle Lamp". Accessed online May 13, 2015. Url: https://blog.naver.com/do6235/220357956988.
(Continued)

*Primary Examiner* — Britt D Hanley
(74) *Attorney, Agent, or Firm* — Novick, Kim & Lee, PLLC; Sang Ho Lee

(57) ABSTRACT

The present invention relates to a candle warmer having a touch type on/off means, which allows a lamp constituting the warmer to flicker by touching a certain portion of a candle body and, more specifically to, a candle warmer having a touch type on/off means, comprising a contact sensor having a dimming function, wherein power supplied to the lamp can be turned on or turned off by bringing the contact sensor into contact with the warmer body to touch a certain portion of the warmer body, and the evaporation loss of an aromatic candle can be controlled by adjusting the output of the lamp.

12 Claims, 2 Drawing Sheets

(51) Int. Cl.
  *F21L 19/00*    (2006.01)
  *F21L 27/00*    (2006.01)
  *F21V 17/12*    (2006.01)
  *F21V 23/04*    (2006.01)
  *F21V 27/02*    (2006.01)
  *F21V 35/00*    (2006.01)
  *H05B 37/02*    (2006.01)

(52) U.S. Cl.
  CPC .............. *F21L 27/00* (2013.01); *F21V 7/041* (2013.01); *F21V 17/12* (2013.01); *F21V 23/04* (2013.01); *F21V 23/0414* (2013.01); *F21V 27/02* (2013.01); *F21V 35/00* (2013.01); *H05B 37/02* (2013.01)

(56) References Cited

FOREIGN PATENT DOCUMENTS

| | | |
|---|---|---|
| KR | 10-1001335 B1 | 12/2010 |
| KR | 10-1391291 B1 | 5/2014 |
| WO | 02/100449 A1 | 12/2002 |

OTHER PUBLICATIONS

Market B product description of "Mantic Candle Lamp GU10". Accessed online Jun. 30, 2017. Url: http://marketb.kr/product/detail.html?product_no=12536&page_6=11#use_qna.

Slog post of "Touch-controlled Stand Sensor replacement". Mar. 20, 2013. Url: http://aat11010.blog.me/60187533213.

Blog post of Pipe Story Candle Warmer. May 30, 2015. Date Accessed: Jun. 13, 2017. Url: http://blog.naver.com/zeissikon/220364967146.

Google image search result for "Candle Warmer" between Jan. 31, 2010-May 30, 2015.

New-Touch Product listing of AC Touch Switch/Dimmer: Date posted: Feb. 19, 2008-Apr. 23, 2010.Url: www.new-touch.com/bbs/zboard.php?id=product_01 & http://www.new-touch.com/bbs/view.php?id=product_01&page=1&sn1=&divpage=1&sn=off&ss=on&sc=on&select_arrange=headnum&desc=asc&no=20 Product description of TD08ZD EMI (small)—Url: http://www.lighttech.co.kr/categoryLS.php?cdl=01.

Safety Korea (Product Safety Information Center) search report of "Dimmer for Illuminator" Model No. TD08ZD EMI. Report date Mar. 29, 2007. Url: http://safetykorea.kr/release/certDetail?certNum=HH11433-7001A&certUid=3010434.

Certification of Compliance issued by the World Standardization Certification & Testing Co., Ltd. for "Touch Switch" by Zhongshan Xiolan Xiongda Electric Appliances Factory. Certified Nov. 26, 2011.

Application for low voltage directive for the World Standardization Certification & Testing Co., Ltd. for "Touch Switch" by Zhongshan Xiolan Xiongda Electric Appliances Factory. Date of report: Nov. 26, 2011.

Product description of "Touch Lamp Control Switch". Accessed Sep. 26, 2017. Url: http://lightingandceilingfans.com/touch-lamp-control-switch-ideas.html.

Youtube video "Lamp Dimmer Switch—Touch Lamp Control" by Fix It Home Improvement Channel. Posted Feb. 20, 2013. Url: https://youtu.be/qysgd6L0x-o.

Youtube video "Bright Image Corporation" by BrightImageCorp. Posted Nov. 13, 2009. Url: https://www.youtube.com/watch?v=hDmjD_3yYTw.

Confirmation of Sale for the product No. 12536 "[Free Halogen bulbs with purchase] Market B Mantic Candle Lamp Touch". Sold since Mar. 13, 2015. Company Name: Market B Co.; Address: 726 Jungmoon-ro, Paju-eup, Paju-si, Gyeonggi-do, Republic of Korea.

* cited by examiner

CANDLE WARMER HAVING TOUCH TYPE ON/OFF MEANS

TECHNICAL FIELD

The present invention relates to a candle warmer for generating fragrance by heating a candle, especially, a scented candle, and more particularly, to a candle warmer having a touch type on/off unit, which allows a lamp of the warmer to be turned on and off when a user touches a certain portion of a warmer body.

More specifically, the present invention relates to a candle warmer having a touch type on/off unit, which includes a contact sensor with a dimming function connected to a warmer body, such that power supplied to a lamp is turned on or off when a user touches a certain portion of the warmer body, and also an amount of evaporation of the scented candle is controlled through a control of output of the lamp.

BACKGROUND ART

In general, a candle is manufactured through the steps of heating stearic acid, paraffin, and hydrogenated oil in a water bath to melt completely, pouring the heated mixture into a mold having a predetermined shape, planting a wick made by twisting cotton, and hardening the mixture by cooling. When a user lights the wick, the candle in a solid state melts to become candle drippings in a liquid state, and the candle burns when the candle drippings turn into a gas state while ascending along the wick.

Such a candle was used as a lighting means in the past, but is now mainly used as a lighting means for emergency or a lighting tool for special events because lighting fixtures using electricity are recently used.

In the meantime, candles with various functions for physical or mental health, called "scented candles", are used in recent times, and there are various technologies including patent document 1 and patent document 2 in connection with such scented candles.

Patent document 1 includes: a first container, which is made of a metallic material with a high heat transfer coefficient, and, in which a paraffin solution having a wick at the middle portion thereof is contained and solidified; a second container, which is spaced apart from the outer contour of the first container at a predetermined interval, and in which the first container is contained; and a mat, which is filled with an incense for generating some fragrance toward the outer contour of the first container and is fit to the outer contour of the first container to be close contact with the first container so as to generate some fragrance through a fumigation action by heat transferred to the outer contour.

Patent document 2 discloses a scented candle consisting of 70% by weight of a paraffin solution which is the main ingredient of the scented candle, and basic materials (natural materials) which consists of 1 to 5% by weight of phytoncide crude liquid, 1 to 5% by weight of a scent selected from an aromatic scent, an orange scent and a herb scent, 1 to 5% by weight of an amethyst powder, 1 to 5% by weight of jade, 1 to 5% by weight of natural dyeing, 1 to 5% by weight of ocher, 1 to 5% by weight of elvan, 1 to 5% by weight of sun stone, 1 to 5% by weight of a pyroligneous liquid, 1 to 5% by weight of an anion material, and a nano silver material of 10 PPM to 950 PPM. The scented candle is made by mixing and stirring the basic materials (natural materials) in the paraffin solution.

Such scented candles are mostly configured such that the scented candle melts and evaporates by fire when a user lights a fire to the wick. However, such scented candles have a risk to cause a fire if the candle with a lit wick falls down or if paper or toilet tissue flies into the candle.

So, recently, candle warmers for indirectly heating a scented candle to evaporate the scented candle have been widely used.

These candle warmers usually have a lamp mounted at one side of a candle holder to generate heat, such that the scented candle is evaporated by heat generated when the lamp is turned on.

However, such conventional candle warmers have a disadvantage in that users may feel inconvenience in operating the lamp because a switch disposed at one side for turning the lamp on may be hidden depending on a direction of the candle warmer.

Moreover, conventional candle warmers, which are configured to simply turn on or off the lamp, may generate too much or too little scent because it cannot control the amount of evaporation of the scented candle.

That is, conventional candle warmers cannot control the amount of evaporation of the scented candle to a desired concentration because the amount of evaporation is fixed even though the amount of evaporation must be increased in a wide space but decreased in a small space.

DISCLOSURE

Technical Problem

Accordingly, the present invention has been made in an effort to solve the above-mentioned problems occurring in the prior arts, and it is an object of the present invention to provide to a candle warmer having a touch type on/off unit, which allows a user to easily turn a lamp of the candle warmer on and off.

Another object of the present invention is to provide such candle warmer having a touch type on/off unit, which also allows the scented candle to evaporate in a desired concentration by controlling the output of the lamp.

Technical Solution

To achieve the above objects, the present invention provides a candle warmer having a touch type on/off unit including: a candle holder for supporting a candle; a lamp which is mounted at one side of the upper part of the candle holder and is operated by receiving electric power to heat the candle such that the candle is evaporated; and a dimming switch mounted inside the candle holder to control the power supply to the lamp such that output of the lamp is controlled by output levels.

Moreover, a switch button is mounted at one side of the candle holder in order to actuate the dimming switch or the dimming switch is actuated by a contact sensor included the dimming switch.

Furthermore, the candle warmer further includes a supporter mounted on an upper portion of the candle holder and a lamp socket disposed at the top of the supporter such that the lamp is detachably mounted.

Additionally, a trumpet-shaped reflector is mounted outside the lamp socket, a bracket is mounted on the outer surface of the reflector, and a fixed screw mounted at the middle of a bracket is fixed to a lampshade mounted at the top of the supporter, such that the lamp socket is fixed to the inside of the lampshade.

Moreover, preferably, the fixed screw protrudes by penetrating through the lampshade, and an assembly knob, which has an outward appearance of a conical shape and a thread formed on the inner surface thereof, is fastened to an end portion of the fixed screw, such that the bracket is fixed to the lampshade.

Furthermore, the lampshade includes a handle. The bottom of the candle holder is open and a support cover is detachably mounted on the open bottom side of the candle holder such that the dimming switch mounted inside the candle holder is easily assembled and disassembled.

Advantageous Effects

As described above, the candle warmer having a touch type on/off unit according to an embodiment of the present invention can allow a user to easily control operation of the candle warmer because the lamp is easily turned on or off when the user touches any one portion of a warmer body.

Additionally, the candle warmer having a touch type on/off unit according to an embodiment of the present invention can allow the user to freely control output of the lamp through the dimming switch, such that the scented candle evaporates and generates fragrance according to the user's desired amount and concentration.

MODE FOR INVENTION

Figure 1:
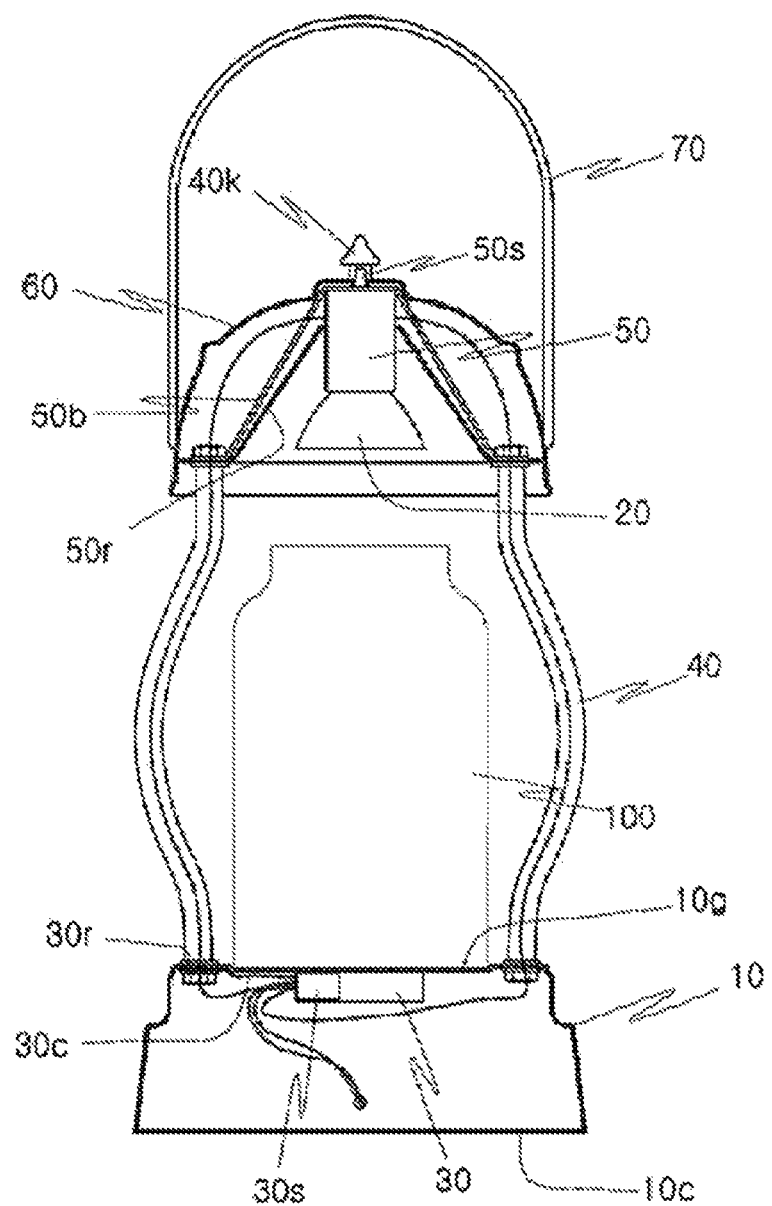
FIG. 1 is a sectional view of a candle warmer having a touch type on/off unit according to an embodiment of the present invention.

The present invention may have example embodiments, which are capable of various modifications and alternative forms, and particular embodiments of the present invention will be illustrated in the attached drawings and described in this specification in detail. It should be understood, however, that there is no intent to limit example embodiments of the invention to the particular forms disclosed, but on the contrary, example embodiments of the invention are to cover all modifications, equivalents, and alternatives falling within the technical idea and scope of the present invention.

In the attached drawings, similar components have similar reference numerals even though they are illustrated in different figures. Additionally, in the description of the present invention, when it is judged that detailed descriptions of known technology related with the present invention may make the essential points vague, the detailed descriptions of the known functions or structures will be omitted.

Hereinafter, reference will be now made in detail to an embodiment of the present invention with reference to the attached drawings.

A candle warmer having a touch type on/off unit according to an embodiment of the present invention can freely control an amount of evaporation of a candle 100 and easily control the operation.

The candle warmer having the touch type on/off unit according to the embodiment of the present invention includes: a candle holder 10 for supporting a candle 100; a lamp 20, which is mounted at one side of the upper part of the candle holder and is operated by receiving electric power to heat the candle such that the candle is evaporated; and a dimming switch 30 mounted inside the candle holder 10 to control the power supply to the lamp such that output of the lamp is controlled by output levels.

Figure 2:
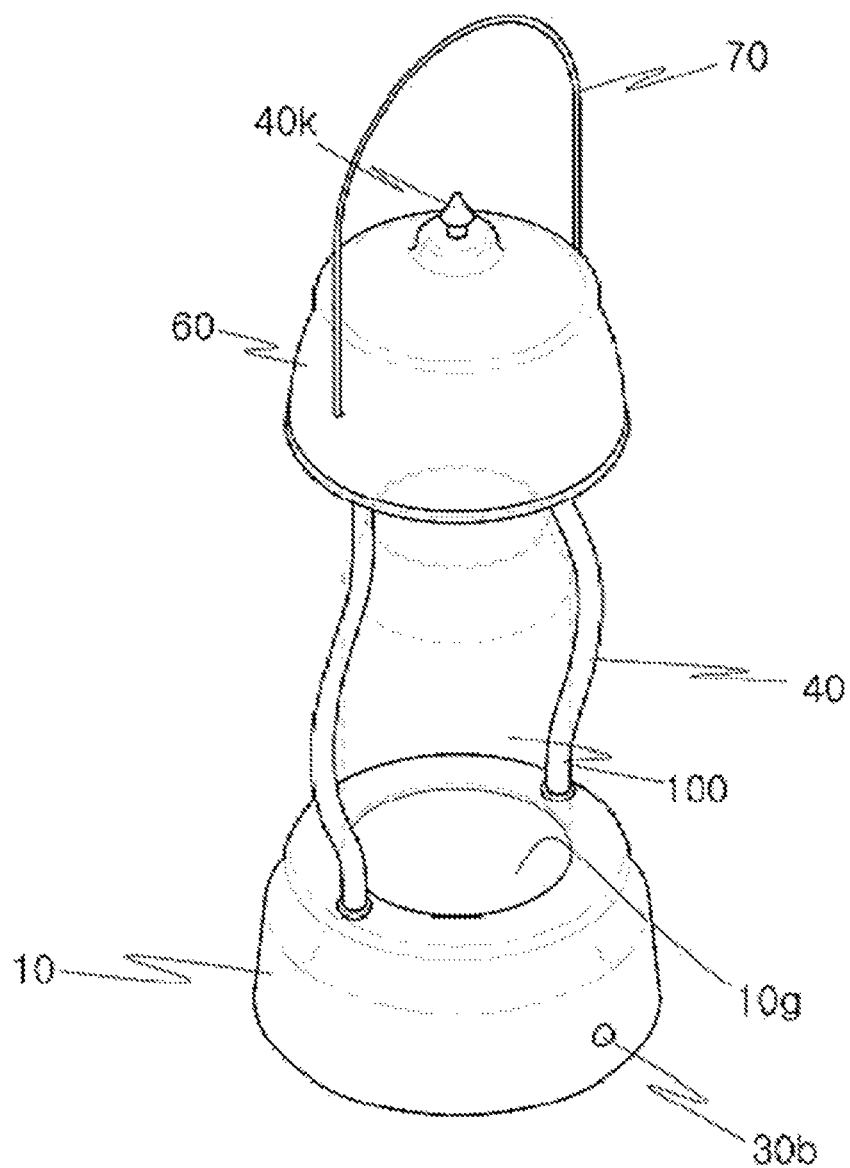
FIG. 2 is a perspective view of the candle warmer having the touch type on/off unit according to the embodiment of the present invention.

As shown in FIGS. 1 and 2, the candle holder 10 serves to hold the candle 100, is a hollow container, and has the dimming switch mounted therein.

The bottom of the candle holder 10 is open, such that the dimming switch mounted therein can be easily assembled and disassembled and a supporter 40 can be easily assembled.

A support cover 10c is detachably mounted on the opened side of the candle holder 10 so as to protect the components mounted in the candle holder.

The support cover 10c is made of an insulating material with bending property, such as synthetic resin or rubber, so as to be detachably attached to the candle holder.

The lamp 20 is turned on by receiving electric power to generate heat, such that the candle 100 is heated and melts and evaporates.

Various kinds of lamps may be used for the lamp 20, but preferably, an LED or a halogen lamp for generating heat at the time of lighting may be used.

The dimming switch 30 is disposed to control the power supply to the lamp 20.

The dimming switch 30 controls power supply to the lamp 20 in order to control output of the lamp. One of generally used dimming switches may be selected.

Various means may be used in order to actuate the dimming switch 30, but as shown in FIG. 2, a switch button 30b is mounted at one side of the candle holder 10 in order to control output of the lamp by controlling electric power supplied to the lamp through the dimming switch according to the number of times the switch button 30b is pushed.

However, in the case that the switch button 30b is mounted at one side of the candle holder 10, it may be difficult for the user to find the small switch button 30b.

Therefore, preferably, a warmer body having the candle holder is made with a conductor and a contact sensor 30s is mounted on the dimming switch 30, such that electric power is supplied to the lamp when a contact is sensed by the contact sensor 30s.

In other words, a sensing cable 30c extending from the contact sensor 30s is connected to the iron body of the candle warmer made of a conductive material, such that the contact sensor senses a contact to control electric power supplied to the lamp when the user touches any portion of the candle warmer.

As described above, the entire body of the candle warmer serves as a contact sensing part, such that an on-off state of the lamp can be controlled more easily. Intensity of illumination of the lamp can be controlled because output of the lamp is controlled according to the number of contact by the user, and an amount of evaporation of the candle 100 is also controlled because heat generated from the lamp is changed.

As shown in FIG. 1, the sensing cable of the contact sensor 30s of the dimming switch can be connected to the bottom surface of the candle holder 10 through a connection ring 30r.

In order to improve the design and function of the candle warmer, the supporter 40 is mounted on the upper portion of the candle holder 10, and a lamp socket 50, on which the lamp is detachably mounted, is mounted at the top of the supporter 40, such that the lamp 20 can be located above the candle 100.

Moreover, a trumpet-shaped reflector 50r is further mounted outside the lamp socket 50, and a bracket 50b is mounted on the outer surface of the reflector. In this instance, a fixed screw 50s mounted at the middle of the bracket 50b is fixed to a lampshade 60 mounted at the top of the supporter, such that the lamp socket is fixed to the inside of the lampshade.

Of course, the supporter 40 penetrates the candle holder 10, and the connection ring 30r is fit to the bottom end of the supporter, which penetrates the candle holder 10, and then, is fastened by a nut, such that the candle holder 10 and the supporter 40 are connected with each other and the sensing cable is connected to the candle holder and the supporter.

Furthermore, the reflector 50r connected to the top of the supporter 40 and the lampshade 60 mounted outside the reflector are also in an electrically connected state. Because the sensing cable 30c is in the electrically connected state, the lamp can be turned on and off even though the user touches the lampshade or the supporter.

Of course, the lamp socket 50 is made of an insulating material, such that it prevents the flow of electric power supplied to the lamp mounted on the lamp socket to the reflector 50r.

As shown in FIG. 1, the supporter 40 is formed in a hollow tube body such that an electric wire for supplying electric power to the lamp can pass therethrough.

Additionally, in order to provide a candle warmer with a more appealing appearance, the candle warmer includes an assembly knob 40k, which is a means for connecting the reflector 50r to the lampshade 60. As shown in FIG. 2, the assembly knob 50k has an outward appearance of a conical shape and a thread formed on the inner surface thereof. So, the assembly knob 40k is fastened to the fixed screw 50s, which penetrates the lampshade, such that the reflector 50r is fixed to the lampshade.

In addition, the lampshade 60 further has a handle 70 so that the user can easily hold and carry the candle warmer.

The invention claimed is:

1. A candle warmer comprising:
a warmer body supporting a candle and made of conductive materials;
a lamp which is mounted at one side of an upper part of the warmer body, is operated by receiving electric power supply, and is disposed away from the candle with a predetermined distance to provide heat to the candle;
a dimming switch being a touch switch and mounted inside the warmer body having a configuration to control the electric power supply and to control output levels of the lamp; and
a contact sensor coupled to each of the dimming switch and the warmer body,
wherein when a user touches any portion of the warmer body, the dimming switch has a configuration to change on-off state or a plurality of output levels of the lamp according to a number of touches by the user and to change an amount of evaporation of the candle in accordance with the plurality of the output levels of the lamp with a use of the contact sensor.

2. The candle warmer of claim 1, wherein a switch button is mounted at one side of the warmer body and adjusts the levels of the dimming switch.

3. The candle warmer of claim 1, wherein the dimming switch comprises a sensing cable connected to the warmer body and the contact sensor.

4. The candle warmer of claim 1, wherein the warmer body comprises a candle holder having a supporter, and a lamp socket disposed at the top of the supporter, and wherein the lamp is detachably mounted on the lamp socket.

5. The candle warmer of claim 4, wherein a trumpet-shaped reflector is mounted outside the lamp socket, a bracket is mounted on an outer surface of the trumpet-shaped reflector, and a fixed screw mounted at the middle of a bracket is fixed to a lampshade mounted at the top of the supporter, and wherein the lamp socket is fixed to the inside of the lampshade.

6. The candle warmer of claim 5, wherein the fixed screw protrudes by penetrating through the lampshade; an assembly knob, which has an outward appearance of a conical shape and a thread formed on the inner surface thereof, is fastened to an end portion of the fixed screw; and the bracket is fixed to the lampshade.

7. The candle warmer of claim 5, wherein the lampshade comprises a handle.

8. The candle warmer of claim 4, wherein the supporter is formed in a hollow tube body and an electric wire supplying electric power to the lamp passes.

9. The candle warmer claim 4, wherein the lamp socket is made of an insulating material and prevents electric power supplied to the lamp of the lamp socket from flowing to the reflector.

10. The candle warmer of claim 4, wherein the bottom of the candle holder is open and a support cover is detachably mounted on the open bottom side of the candle holder and the dimming switch mounted in the supporter is assembled and disassembled.

11. A candle warmer comprising:
a warmer body supporting a candle and made of conductive materials;
a lamp which is mounted at one side of an upper part of the warmer body, is operated by receiving electric power supply, and is disposed away from the candle with a predetermined distance to provide heat to the candle;
a dimming switch being a touch switch and mounted inside the warmer body having a configuration to control the electric power supply and to control output levels of the lamp; and
a contact sensor coupled to each of the dimming switch and the warmer body,
wherein when a user touches any portion of the warmer body, the dimming switch has a configuration to change on-off state or a plurality of output levels of the lamp according to a number of touches by the user and to change an amount of evaporation of the candle in accordance with the plurality of the output levels of the lamp with a use of the contact sensor,
wherein the warmer body comprises a candle holder having a supporter, and a lamp socket disposed at the top of the supporter, and wherein the lamp is detachably mounted on the lamp socket, and
wherein a trumpet-shaped reflector is mounted outside the lamp socket, a bracket is mounted on an outer surface of the trumpet-shaped reflector, and a fixed screw mounted at the middle of a bracket is fixed to a lampshade mounted at the top of the supporter, and wherein the lamp socket is fixed to the inside of the lampshade.

12. A candle warmer comprising:
a warmer body supporting a candle and made of conductive materials;
a lamp which is mounted at one side of an upper part of the warmer body, is operated by receiving electric power supply, and is disposed away from the candle with a predetermined distance to provide heat to the candle;

a dimming switch being a touch switch and mounted inside the warmer body having a configuration to control the electric power supply and to control output levels of the lamp; and a contact sensor coupled to each of the dimming switch and the warmer body, wherein when a user touches any portion of the warmer body, the dimming switch has a configuration to change on-off state or a plurality of output levels of the lamp according to a number of touches by the user and to change an amount of evaporation of the candle in accordance with the plurality of the output levels of the lamp with a use of the contact sensor, wherein the warmer body comprises a candle holder having a supporter, and a lamp socket disposed at the top of the supporter, and wherein the lamp is detachably mounted on the lamp socket, wherein a trumpet-shaped reflector is mounted outside the lamp socket, a bracket is mounted on an outer surface of the trumpet-shaped reflector, and a fixed screw mounted at the middle of a bracket is fixed to a lampshade mounted at the top of the supporter, and wherein the lamp socket is fixed to the inside of the lampshade, wherein the fixed screw protrudes by penetrating through the lampshade; an assembly knob, which has an outward appearance of a conical shape and a thread formed on the inner surface thereof, is fastened to an end portion of the fixed screw; and the bracket is fixed to the lampshade, wherein the lampshade comprises a handle, wherein the supporter is formed in a hollow tube body and an electric wire supplying electric power to the lamp passes, wherein the lamp socket is made of an insulating material and prevents electric power supplied to the lamp of the lamp socket from flowing to the reflector, wherein the bottom of the candle holder is open and a support cover is detachably mounted on the open bottom side of the candle holder and the dimming switch mounted in the supporter is assembled and disassembled.

* * * * *